US005821106A

United States Patent [19]
Chung et al.

[11] Patent Number: 5,821,106
[45] Date of Patent: Oct. 13, 1998

[54] CDNA OF DIRECT-ACTING FIBRINOLYTIC SERINE PROTEASE

[75] Inventors: Kwang-Hoe Chung, Kyonggi-Do; You-Seok Koh, Seoul; Jae-Hoon Hwang, Seoul; Doo-Sik Kim, Seoul; Yung-Dae Yun, Seoul; Hong-Mo Moon, Kyonggi-Do, all of Rep. of Korea

[73] Assignee: Mogam Biotechnology Research Institute, Kyonggi-Do, Rep. of Korea

[21] Appl. No.: 738,413

[22] Filed: Oct. 25, 1996

[30] Foreign Application Priority Data

Jun. 21, 1996 [KR] Rep. of Korea .................. 96 23013

[51] Int. Cl.$^6$ .............................. C12N 9/64; C12N 15/57
[52] U.S. Cl. .......................................... 435/226; 536/23.2
[58] Field of Search ............................ 435/226; 536/23.2

[56] References Cited

U.S. PATENT DOCUMENTS 4,568,545  2/1986  Mihara et al. ..................... 424/94.64

FOREIGN PATENT DOCUMENTS 707067  4/1996  European Pat. Off. .

OTHER PUBLICATIONS

Hung, C.-C., et al., Biochemical and Biophysical Research Communications, vol. 205, "Characterization of one novel venon protease with beta–fibrinogenase activity from the Taiwan habu: purification and cDNA sequence analysis", pp. 1707–1715. 1994.

Nikai, T., et al., Archives of Biochemistry and Biophysics, vol. 318, "Primary structure of a coagulane enzyme, bilineobin, from Agkistrodon bilineatus venom", pp. 89–96. 1995.

Fujimura, S., et al., Biochimica et Biophysica Acta, vol. 1243, "Purification and chararterization of a non–hemorrhagic metalloprotease from Agkistrodon halys brevicaudus venom", pp. 94–100. 1995.

Deshimaru, M., et al., FEBS Letters, vol. 397, "Accelerated evolution of crotalinae snake venom gland serine proteases", pp. 83–88. 1996.

Kisiel, W., et al., The Journal of Biological Chemistry, vol. 262, "Chracterization of a protein C activator from Agkistrodon contortrix contortrix venom", pp. 12607–12613. 1997.

Lijnen, H.R. & Collen, D. *Strategies for the improvement of Thrombolytic Agents,* Tromb.Haemost., 66:88–110 (1991).

Sawyer, R.T. *Thrombolytics and Anticoagulants from Leeches,* Bio/Technology, 9:513–518 (1991).

Gardell, S.J. et al., *Isolation, Characterization, and cDNA Cloning. . . ,* J.Biol.Chem., 264:17947–17952 (1989).

Meier, J. & Stocker, K. *Effects of Snake Venoms on Haemostasis,* CRC Critical Reviews in Toxicology (1991).

Siigur, E. & Siigur, Jr., *Purification and Characterization of Lebetase. . . ,* Biochem.Biophys.Acta., 1074:223–229 (1991).

(List continued on next page.)

*Primary Examiner*—Eric Grimes
*Assistant Examiner*—William W. Moore
*Attorney, Agent, or Firm*—Darby & Darby

[57] ABSTRACT

The present invention relates to a novel cDNA of direct-acting fibrinolytic serine protease ("Salmonase") which is prepared from a Korean viper, Salmosa(*Agkistrodon halys brevicaudus*), and a direct-acting fibrinolytic serine protease deduced therefrom. The cDNA of direct-acting fibrinolytic serine protease contains 699 nucleotides coding for 233 amino acids, and the Salmonase translated therefrom consists of two subunits of 77 and 156 amino acids, respectively. Salmonase cDNA of the invention may be expressed in the proper systems established in the recombinant *E. coli*, yeast, baculovirus/insect cells and other animal cells, and the recombinant Salmonase prepared therefrom can be practically applied as an active ingredient of thrombolytic and hemostatic agents.

4 Claims, 5 Drawing Sheets

OTHER PUBLICATIONS

Randolph, A. et al., *Amino Acid Sequence of Fibrolase*. . . Protein Science, 1:590–600 (1992).

Stocker, K.F. *Medical Use of Snake Venom Proteins,* CRC Press, Boca Raton Ann Arbor Boston, pp. 136–140 (1992).

Willis, T.W. & Tu, A.T. *Purification and Biochemical Characterization of Atroxase.* . . , Biochemistry, 27:4769–4777 (1988).

Chung, K.H. & Kim, D.S. *Purification and Characterization of a Fibrinolytic Enzyme from Korean Snake.* . . , Korean Biochem. J., 26:363–369 (1993).

Chung, K.H. et al. *Biochemical and Biological Properties.* . . , Korean Biochem., Jr., 26:370–377 (1993).

Chung, K.H. et al. *Fibrinolytic and Coagulation Activities.* . . , Korean Biochem.J. 25:696–701 (1992).

Chung, K.H. et al. *A Fibrin(ogen)olytic Enzyme* . . . , Thrombo. Haemost. THHADQ, 65:953 (1991).

Hahn, B.S. et al. *Purification and Molecular Cloning* . . . , J.Biochem., 119:835–843 (1996).

Itoh, N. et al. *Organization of the Gene for Batroxobin.* . . , J.Biol. Chem., 263:7628–7631 (1988).

Zhang, Y. et al. *A Novel Plasminogen Activator from Snake Venom,* J.Biol. Chem., 270 10246–10255 (1995).

Xiaohong, Q. et al. *Fibrinolytic Enzyme from Agkistrodon halys.* . . , Toxicon, 29:1381–1386 (1991).

FIG. 2

```
  1 GTCATTGGAG GAGACGAATG TAACATAAAT GAACATCGTT TCCTTGCACT CCTGTACTCT
 61 GAGAGGTTTC AATGCGGGTGG GACTTTGATC AACGAAGAAT GGGTGCTCAC CGCTGCACAC
121 TGCGACATGA GAAATATGTA CATATACCTT GGTGTGCATA ACGTAAGTGT ACAATACGAT
181 GATGAGCAGA GAAGATACCC AAAGAAGAAG CACTTTCGCC TCAGTAGCAG AAACTATAAC
241 CAATGGGACA AGGATATCAT GTTGATCAGA TTGAACAGAC CTCTTAGGAA CAGTGCACAC
301 ATCGCGCCTC TCAGCTTGCC TTCCAACCCT CCCAGTGTGT TCTCAGTTTG CCGTATTATG
361 GGATGGGGCA CAATCACATC TCCTCAAGTG ACTTTTCCCG ATGTCCTTCA CTGTGCTAAC
421 ATTAACATTT TGATTATGA GGTGTGTCGA GCAGCTTACC CAGAGTTGCC AGCAACAAGG
481 AGAACATTGT GTGCAGGTAT CCTGGAAGGA GGCAAAGATT CATGTAACGG TGACTCTGGG
541 GGACCCCTCA TCTGTAATGG ACAATTCCAG GGCATTGCAT ATTGGGGGGC CGATACTTGT
601 GCCCAACCGC GTGAGCCTGG CCCTCTACACC AAGGTCTTTG ATTATATTGA TTGGATCCAA
661 AGCATTATTG CAGGAAATAC AGCTGTGACT TGCCCC
```

```
                       10         20         30         40         50
                        #                     #          $#
SALMONASE    1 VIGGDECNIN EHRFLALLYS ---ERFQCGG TLINEEWVLT AAHCDMRNMY
FLAVOXOBIN   1 *****D PVAD AWSGL* P* ***SK*FK
BATROXOBIN   1 ******D PFM*Y --SP*YFM Q* **NR*F*R
ANCROD       1 ******** **VAV*E GTNWT*I* VHP***I* *E**AR*R*N 60         70         80         90        100
                                              *          $
SALMONASE   51 IYLGVHNVSV QYDDEQRRYP KKKY-FRLSS R-NYNQWDKD IMLIRLNRPL
FLAVOXOBIN  51 MK**A*SQK* LNE***I*N* *E*--*ICPN KK*TEVL*** ****K*DS*V
BATROXOBIN  51 *H**K*TR ANYVV*** *E*---*ICPN KKKNVIT* **DV
ANCROD      51 LVF*M*RK*E KF**E* **R*FI*CNK TR--TS**E* *******K*V 110        120        130        140        150
                                              #                   #
SALMONASE  101 RNSAHIAPLS LPSNPPSVFS VCRIMGWGTI TSPQVTFPDV LHCANINIFD
FLAVOXOBIN 101 SY*E**** *S*****G* ********S* *PVEE*** P***LL*
BATROXOBIN 101 KE** *******G* ********A* *TSED*Y* P***L*N
ANCROD     101 NE** ****I*G* DV**S* NRRIDVLS*E PR****LHN
```

FIG. 4B

```
              160        170        180        190        200
SALMONASE 151 YEVCRAAYPE LPATRRTLCA GILEGGKDSC QGDSGGPLIC NGQFQGIAYW
FLAVOXOBIN 151 DVE*KPG*** *LPEY**** *V*Q**I*T* GF***T*** ******V*I
BATROXOBIN 151 NT*ENG *--K** *V*Q**I*T* G******* ****LS*
ANCROD    151 FTM*HGLFRK M*KKG*V*** *D*R*RR*S* NS******** *EELH**VAR 210        220        230        240        250
SALMONASE 201 GADTCAQPRE PGLYTKVFDV IDWIQSIIAG NTAVTCP.. ..........
FLABOXOBIN 201 *SHP*G*S*K I*** NA**** *A**LP.. ..........
BATROXOBIN 201 *S*PEK *AF***** LP****** *KTA***.. ..........
ANCROD    201 *PNP****NK *A*SIY RVNNV* *--A**SP.. ..........
```

CDNA OF DIRECT-ACTING FIBRINOLYTIC SERINE PROTEASE

FIELD OF THE INVENTION

The present invention relates to a novel cDNA of direct-acting fibrinolytic serine protease, more specifically, to a novel CDNA of direct-acting fibrinolytic serine protease which is prepared from a Korean viper, Salmosa (*Agkistrodon halys* brevicaudus), and a direct-acting fibrinolytic serine protease deduced therefrom.

BACKGROUND OF THE INVENTION

Thrombosis and hemostasis have been a principal subject in the medical field for a long time. In this regard, studies on the thrombolytic agents such as urokinase, streptokinase and tissue-type plasminogen activator, etc., have been actively carried out, and their use as therapeutic agents for thrombosis has been also practiced (see: Lijnen, H. R. and Collen, D., Thromb. Haemost., 66:88(1991)). Recently, a variety of biologically active materials have been isolated from natural sources such as leeches, vampire bats and snake venoms, etc., and applied in the control of thrombosis (see: Sawyer, R. T., Bio/Technology, 9:513(1991); U.S. Pat. No. 4,568,545; Gardell S. J. et al., J. Biol. Chem., 264:17947(1989); Meier, J. and Stocker, K., CRC Critical Reviews in Toxicology, 21:171(1991); Siigur, E. and Siigur, J., Biochim. Biophys. Acta, 1074:223(1991); Randolph, A. et al., Protein Science, 1:590(1992)).

Under the circumstances, snake venoms which have been reported to affect human hemostatic system have been studied considerably, and many components in the venoms having effects on the hemostatic system have been isolated and characterized. Among them, some substances have been practically used for basic research, diagnosis and treatment, etc., and a variety of snake venoms having the activity of thrombin-like serine protease which cleaves fibrinopeptide to convert fibrinogen to fibrin has been reported (see: Meier, J. and Stocker, K., CRC Critical Reviews in Toxicology, 21:171(1991)). Presently, 23 thrombin-like serine proteases have been identified, and amino acid sequences of four proteases among them have been fully determined.

Particularly, the enzymatic properties of Batroxobin have been well characterized: that is, Batroxobin is a thrombin-like serine protease isolated from the venom of *Bothrops atrox* moojeni, commonly called Lance head snake, and it cleaves only fibrinopeptide A of fibrinogen. Even a small amount of Batroxobin is able to convert fibrinogen to fibrin I(Des-A-fibrin) which is degraded rapidly by plasmin, which finally results in a decrease of fibrinogen level in blood. Generally, it can induce the synthesis of plasminogen activator and accelerate degradation of thrombus, but a high level of Batroxobin rather causes blood clotting. Grounded on the biochemical properties, Batroxobin has been developed as a defibrinogenating drug (commercial name "Defibrase") and as a hemostatic agent (commercial name "Reptilase") as well (see: Meier, J. and Stocker, K., Medical Use of Snake Venom Proteins, CRC Press, p.136(1990)).

Fibrinolytic proteases as well as thrombin-like serine proteases exist in the snake venoms, and some of which have been characterized at a molecular level. For example, Atroxase isolated from Western Diamondback Rattle Snake venom having a molecular weight of 23,500 dalton has been reported as a single-chain basic protein (pI: 9.6) consisting of 206 amino acids(see: Willis, T. W. and Tu, A. T., Biochemistry, 27:4769(1988)). Particularly, Atroxase has been suggested to be a kind of metalloproteinase, since it has no cysteine residue and contains a metal ion, i.e., zinc. In addition, Fibrolase isolated from the venom of *Agkistrodon contoritrix*, has been reported as a single-chain metalloproteinase having a molecular weight of 22,891 dalton, which consists of 203 amino acids and contains 6 cysteine residues (see: Randolph, A. et al., Protein Science, 1:590(1992)). Also, Lebetase isolated from *Vipera lebetina* has been known as a single-chain metalloproteinase consisting of 214 amino acids(see: Siigur, E. and Siigur, J., Biochim. Biophys. Acta, 1074:223(1991)).

On the other hand, it has been reported that only 3 species of Agkistrodon genus, among 14 species of Korean snakes, have venoms (see: Nah, K. Y., Kor. J. Surgery, 17:13(1975); Gloyd, H. K., Proc. Biol. Soc. Washington, 85:557(1971)). A fibrinolytic protease firstly identified in the venom of *Agkistrodon halys* brevicaudus, has been known as a single-chain glycoprotein having a molecular weight of 39,200 dalton, which consists of 323 amino acids and contains a lot of glutamic acids and aspartic acids (see: Sun, J. et al., Chem. Abstr., 108:90629n(1988)). A fibrinolytic protease having a molecular weight of 51,000 dalton has been also isolated from *Agkistrodon halys* brevicaudus (see: Chung, K. H. and Kim, D. S., Thromb. Haemost. THHADQ, 65:953 (1991)).

In line with these reports, the present inventors have reported a direct-acting fibrinolytic serine protease having a molecular weight of 31,000 dalton, which is isolated from the venom of *Agkistrodon halys* brevicaudus, and found that it is a novel serine protease possessing higher activity than the said fibrinolytic protease having a molecular weight of 51,000 dalton. In this regard, the inventors named the serine protease 'Salmonase' for convenience, and clarified its structural properties that it is a glycoprotein consisting of two subunits each of which has a molecular weight of 16,000 dalton and 17,000 dalton, which are cross-linked by a disulfide bond (see: Korean Unexamined Patent Publication No. 95-871).

SUMMARY OF THE INVENTION

In accordance with the present invention, the inventors have cloned cDNA of Salmonase, a direct-acting fibrinolytic protease from cDNA library of the venom gland of a Korean viper, Salmosa(*Agkistrodon halys* brevicaudus), and discovered that its nucleotide sequence and amino acid sequence deduced therefrom are novel.

The primary object of the present invention is, therefore, to provide a novel cDNA of a direct-acting fibrinolytic protease("Salmonase"), which is originated from the venom gland of Salmosa(*Agkistrodon halys* brevicaudus).

The other object of the invention is to provide a direct-acting fibrinolytic protease ("Salmonase") having amino acid sequence deduced from the cDNA.

BRIEF DESCRIPTION OF THE DRAWINGS

The above and the other objects and features of the present invention will become apparent from the following descriptions given in conjunction with the accompanying drawings, in which:

FIG. 2 shows nucleotide sequence (SEQ ID No: 8) of cDNA of Salmonase.

FIG. 3 shows amino acid sequence (SEQ ID No: 9) translated from the cDNA as shown in FIG. 2.

FIG. 4 shows the comparison of amino acid sequences (SEQ ID No: 10; SEQ ID No: 11; and, SEQ ID No: 12) between Salmonase and known serine proteases from venom glands.

DETAILED DESCRIPTION OF THE INVENTION

Figure 1:
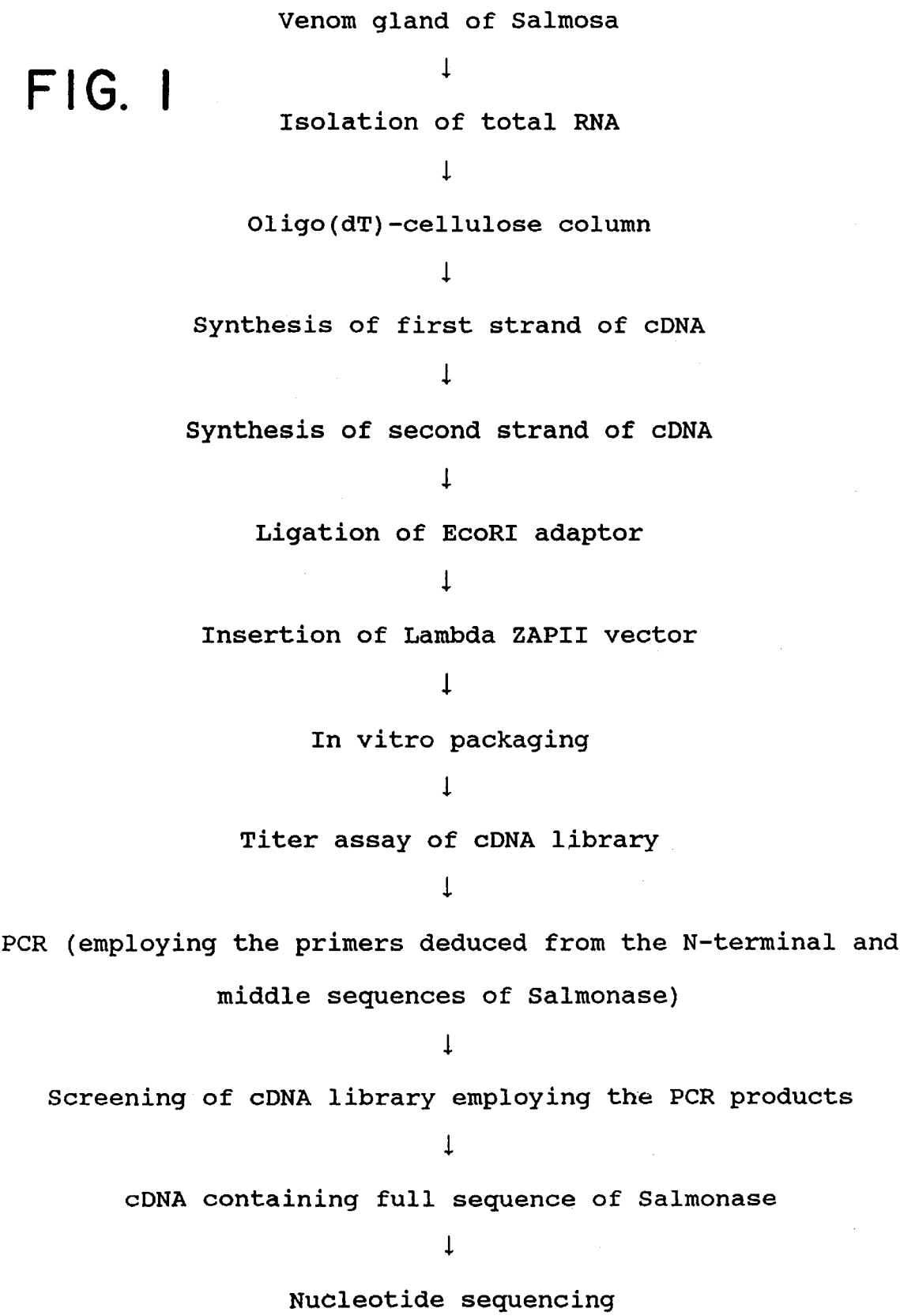
FIG. 1 is a schematic diagram showing the construction strategy of a cDNA library of the venom gland of Salmosa (*Agkistrodon halys* brevicaudus).

The inventors have cloned cDNA of Salmonase by the aid of polymerase chain reaction ("PCR") which employs oligonucleotide primers for the N-terminal amino acid sequences of two subunits of a serine protease isolated from the venom gland of *Agkistrodon halys* brevicaudus, and the cDNA library of the venom gland as the template. Cloned cDNA contains 699 nucleotides coding for 233 amino acids, and the protein translated therefrom consists of two subunits of 77 and 156 amino acids, respectively. Estimated from the deduced amino acid sequence, it was determined that Salmonase has a molecular weight of 26 kDa, including one N-glycosylation site.

On the other hand, based on the sequence homology studies, it has been revealed that Salmonase shows 54 to 68% homology to known serine proteases, in light of amino acid sequence. Moreover, it has been found that Salmonase of the invention, like the known enzymes, conserves His, Asp, Ser and their adjacent amino acid sequences constituting the active site of the serine protease, and N-terminal amino acid sequence as well. Particularly, it was revealed that eleven of 12 cysteines conserved in all of the serine proteases were conserved well. Since one cysteine was not conserved at the position of the 74th amino acid, it was suggested that the 74th amino acid, along with the 77th amino acid of arginine which is the cleavage site to give two subunits, may play an important role in the formation of dimer.

A novel Salmonase cDNA of the invention originated from the venom gland of *Agkistrodon halys* brevicaudus may be expressed in the proper systems established in the recombinant *E. coli*, yeast, baculovirus/insect cells and other animal cells, and the recombinant Salmonase prepared therefrom can be practically applied as an active ingredient of thrombolytic and hemostatic agents.

The present invention is further illustrated in the following examples, which should not be taken to limit the scope of the invention.

EXAMPLE 1

Construction of cDNA library from the venom gland of a Korean viper, Salmosa(*Agkistrodon halys* brevicaudus)

The venom glands were obtained from a Korean viper, Salmosa(*Agkistrodon halys* brevicaudus). As the venom gland is a pea-like tiny organ, at least five glands were used to obtain a sufficient amount of RNA. To isolate total cellular RNA, guanidine isothiocyanate was treated, and ultracentrifugation with CsCl cushion followed. Then, poly(A)+ RNA was separated from the total cellular RNA, by applying on oligo(dT) -cellulose column twice, and first and second strands of cDNA were synthesized by employing reverse transcriptase, RNase H and *E. coli* DNA polymerase I (see: Sambrook et al., Molecular Cloning, 2nd Ed., Cold Spring Harbor Laboratory (1989)). Ligation of an appropriate adaptor to the cDNA thus synthesized, insertion into lambda ZAPII (Stratagene, U.S.A.) and in vitro packaging were successively carried out to construct cDNA library. cDNA library thus constructed was determined to contain $10^6$ independent plaques. The construction strategy of the cDNA library from the venom gland of a Korean viper, Salmosa was schematically depicted in FIG. 1.

EXAMPLE 2

Cloning of Salmonase cDNA

Salmonase cDNA was cloned from the cDNA library prepared in Example 1 as followings.

In order to clone the larger one of the two subunits of Salmonase, a degenerated oligonucleotide having the sequence of 5'-AA(T/C)TA(T/C)AA(T/C)CA(A/G)TTG-3' (SEQ ID No: 1) was employed as 5'-primer, based on NYNQW (SEQ ID No: 2) of N-terminal region of the larger subunit, and a degenerated oligonucleotide having the sequence of 5'-AT(A/T/G)ATGCT(C/T)TG(A/T/G)CA(A/G)TC-3' (SEQ ID No: 3) was employed as 3'-primer, based on DWIQSII (SEQ ID No: 4) of C-terminal region of the serine protease. PCR was carried out using the said primers, Taq DNA polymerase and the cDNA library prepared in Example 1 as the template to obtain 450 bp-PCR product. In this connection, denaturation (94° C., 30 seconds), annealing(39° C., 1 minute) and extension (72° C., 1 minute) were carried out for 30 cycles in a serial manner. The PCR product thus obtained was subcloned on plasmid pCRII (Invitrogen, U.S.A.), and its nucleotide sequence was determined.

In addition, in order to clone the smaller one of the two subunits of Salmonase, a degenerated oligonucleotide having the sequence of 5'-GTIATIGGIGGNGA(T/C)GA(A/G)TG-3' (SEQ ID No: 5) was employed as 5'-primer, based on VIGGDEC (SEQ ID No: 6) of N-terminal region of the smaller subunit (wherein, I represents inosine; and, N represents A, G, C or T, respectively), and an oligonucleotide having the sequence of 5'-TT(A/G)AT(A/G)TT(A/G)GT(T/C)AAC-3' (SEQ ID No: 7), the complementary sequence for the degenerated oligonucleotide prepared, based on the previously used NYNQW(SEQ ID No: 2), was employed as 3'-primer. PCR was carried out using the said primers, Taq DNA polymerase and the cDNA library prepared in Example 1 as the template, finally to obtain 250 bp-PCR product. In this connection, denaturation (94° C., 30 seconds), annealing (48° C., 1 minute) and extension (72° C., 30 seconds) were carried out for 30 cycles in a serial manner. The PCR product thus obtained was subcloned on plasmid pCRII (Invitrogen, U.S.A.), and its nucleotide sequence was determined.

EXAMPLE 3

Determination and analysis of DNA sequence

The nucleotide sequences of the PCR products obtained in Example 2 were determined employing Sequenase (USB, U.S.A.) and primers derived from the vector and cDNA sequence by the dideoxy nucleotide termination method(see: Sambrook et al., Molecular Cloning, 2nd Ed., Cold Spring Harbor Laboratory (1989)).

Figure 3:
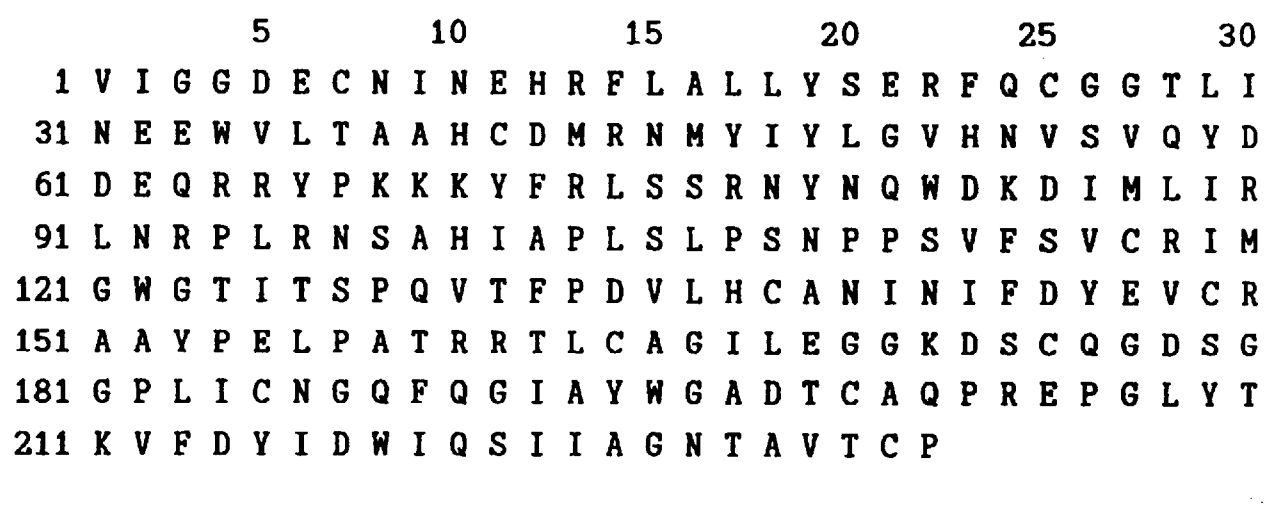

Based on the results from nucleotide sequencing of Salmonase cDNA (SEQ ID No: 8) and analysis of its deduced amino acid sequence (SEQ ID No: 9) (see: FIGS. 2 and 3), it was found that Salmonase CDNA has 699 nucleotides coding for 233 amino acids, and Salmonase consisting of 233 amino acids is a mature enzyme having two subunits each of which consists of 77 amino acids (i.e., 1st to 77th amino acid) and 156 amino acids (i.e., 78th to 233th amino acid). Also, based on the amino acid sequence, the mature enzyme was assumed to be a glycoprotein which has a higher molecular weight in the viper venom than 26 kDa, since it contains one N-glycosylation site, and, based on the composition analysis of the amino acids, its isoelectric point (pI) was determined to be 5.04.

On the other hand, the sequence homology was searched by using Swiss-Prot program, which revealed that the translated amino acid sequence from Salmonase cDNA displays 54 to 68% homology to those of known serine proteases, i.e., FLAVOXOBIN (see: Shieh, T. C. et al., J. Biochem., 103:596(1988)) (SEQ ID No: 10), BATROXOBIN (see: Itoh, N. et al., J. Biol. Chem., 263 :7628(1988)) (SEQ ID No: 11) and ANCROD(see: Hatton, M. W. C., Biochem. J., 131:799(1973)) (SEQ ID No: 12) (see: FIG. 4). In FIG. 4, '*', '$' and '#' represent the conserved amino acid, the active site and the conserved cysteine residue, respectively.

Moreover, it was found that Salmonase of the invention has His, Asp, Ser (represented as '$' in FIG. 4) and their adjacent amino acid sequences constituting the active site of the serine protease, and N-terminal amino acid sequence which are well conserved like the known enzymes. Particularly, it was revealed that eleven (represented as '#' in FIG. 4) of 12 cysteines appeared in all of serine proteases are conserved well. Also, the fact that the 74th amino acid is not conserved cysteine residue and the 77th arginine proposed to be a cleavage site in the mature enzyme, resulted in the structural distinction of Salmonase consisting of two subunits over other enzymes.

As clearly illustrated and demonstrated as above, the present invention provides a novel cDNA of direct-acting fibrinolytic serine protease which is originated from the venom gland of a Korean viper, Salmosa(*Agkistrodon halys brevicaudus*), and a direct-acting fibrinolytic serine protease deduced therefrom. Salmonase cDNA contains 699 nucleotides coding for 233 amino acids, and the protein translated therefrom consists of two subunits consisting of 77 and 156 amino acids, respectively. Salmonase cDNA of the invention may be expressed in the proper systems established in the recombinant *E. coli*, yeast, baculovirus/insect cells and other animal cells, and the recombinant Salmonase prepared therefrom can be practically applied as an active ingredient of thrombolytic and hemostatic agents.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 5'PCR primer ( x i ) SEQUENCE DESCRIPTION: SEQ ID NO:1:

A A Y T A Y A A Y C   A R T T G                      1 5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Agkistrodon halys brevicaudus ( x i ) SEQUENCE DESCRIPTION: SEQ ID NO:2:

Asn  Tyr  Asn  Gln  Trp
        1                       5

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 3'PCR primer ( x i ) SEQUENCE DESCRIPTION: SEQ ID NO:3:

A T D A T G C T Y T   G D C A R T C                    1 7

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Agkistrodon halys brevicaudus ( x i ) SEQUENCE DESCRIPTION: SEQ ID NO:4:

Asp Trp Ile Gln Ser Ile Ile
        1                  5

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 5'PCR primer ( i x ) FEATURE:
        ( A ) NAME/KEY: modified_base
        ( B ) LOCATION: one-of(3, 6, 9)
        ( C ) IDENTIFICATION METHOD: experimental
        ( D ) OTHER INFORMATION:/evidence=EXPERIMENTAL
            / frequency= 0.15
            / mod_base= i
            / label= N ( x i ) SEQUENCE DESCRIPTION: SEQ ID NO:5:

GTNATNGGNG GNGAYGARTG                    20

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Agkistrodon halys brevicaudus ( x i ) SEQUENCE DESCRIPTION: SEQ ID NO:6:

Val Ile Gly Gly Asp Glu Cys
        1                  5

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 3'PCR primer ( x i ) SEQUENCE DESCRIPTION: SEQ ID NO:7:

```
            TTRATRTTRG TYAAC                                                           15
```

( 2 ) INFORMATION FOR SEQ ID NO:8:

( i ) SEQUENCE CHARACTERISTICS:
    ( A ) LENGTH: 699 base pairs
    ( B ) TYPE: nucleic acid
    ( C ) STRANDEDNESS: single
    ( D ) TOPOLOGY: linear ( i i ) MOLECULE TYPE: cDNA to mRNA ( v i ) ORIGINAL SOURCE:
    ( A ) ORGANISM: Agkistrodon halys brevicaudus ( v i i ) IMMEDIATE SOURCE:
    ( B ) CLONE: protease ( x i ) SEQUENCE DESCRIPTION: SEQ ID NO:8:

```
GTCATTGGAG  GAGACGAATG  TAACATAAAT  GAACATCGTT  TCCTTGCACT  CCTGTACTCT       60
GAGAGGTTTC  AATGCGGTGG  GACTTTGATC  AACGAAGAAT  GGGTGCTCAC  CGCTGCACAC      120
TGCGACATGA  GAAATATGTA  CATATACCTT  GGTGTGCATA  ACGTAAGTGT  ACAATACGAT      180
GATGAGCAGA  GAAGATACCC  AAAGAAGAAG  CACTTTCGCC  TCAGTAGCAG  AAACTATAAC      240
CAATGGGACA  AGGATATCAT  GTTGATCAGA  TTGAACAGAC  CTCTTAGGAA  CAGTGCACAC      300
ATCGCGCCTC  TCAGCTTGCC  TTCCAACCCT  CCCAGTGTGT  TCTCAGTTTG  CCGTATTATG      360
GGATGGGGCA  CAATCACATC  TCCTCAAGTG  ACTTTTCCCG  ATGTCCTTCA  CTGTGCTAAC      420
ATTAACATTT  TTGATTATGA  GGTGTGTCGA  GCAGCTTACC  CAGAGTTGCC  AGCAACAAGG      480
AGAACATTGT  GTGCAGGTAT  CCTGGAAGGA  GGCAAAGATT  CATGTAACGG  TGACTCTGGG      540
GGACCCCTCA  TCTGTAATGG  ACAATTCCAG  GGCATTGCAT  ATTGGGGGGC  CGATACTTGT      600
GCCCAACCGC  GTGAGCCTGG  CCTCTACACC  AAGGTCTTTG  ATTATATTGA  TTGGATCCAA      660
AGCATTATTG  CAGGAAATAC  AGCTGTGACT  TGCCCCCCA                                699
```

( 2 ) INFORMATION FOR SEQ ID NO:9:

( i ) SEQUENCE CHARACTERISTICS:
    ( A ) LENGTH: 233 amino acids
    ( B ) TYPE: amino acid
    ( C ) STRANDEDNESS: Not Relevant
    ( D ) TOPOLOGY: Not Relevant ( i i ) MOLECULE TYPE: protein ( v i ) ORIGINAL SOURCE:
    ( A ) ORGANISM: Agkistrodon halys brevicaudus ( v i i ) IMMEDIATE SOURCE:
    ( B ) CLONE: protease - aa ( x i ) SEQUENCE DESCRIPTION: SEQ ID NO:9:

```
Val  Ile  Gly  Gly  Asp  Glu  Cys  Asn  Ile  Asn  Glu  His  Arg  Phe  Leu  Ala
 1              5                         10                         15

Leu  Leu  Tyr  Ser  Glu  Arg  Phe  Gln  Cys  Gly  Gly  Thr  Leu  Ile  Asn  Glu
             20                         25                         30

Glu  Trp  Val  Leu  Thr  Ala  Ala  His  Cys  Asp  Met  Arg  Asn  Met  Tyr  Ile
             35                         40                         45

Tyr  Leu  Gly  Val  His  Asn  Val  Ser  Val  Gln  Tyr  Asp  Asp  Glu  Gln  Arg
             50                         55                         60

Arg  Tyr  Pro  Lys  Lys  Lys  Tyr  Phe  Arg  Leu  Ser  Ser  Arg  Asn  Tyr  Asn
 65                       70                         75                         80
```

```
Gln  Trp  Asp  Lys  Asp  Ile  Met  Leu  Ile  Arg  Leu  Asn  Arg  Pro  Leu  Arg
               85                      90                       95

Asn  Ser  Ala  His  Ile  Ala  Pro  Leu  Ser  Leu  Pro  Ser  Asn  Pro  Pro  Ser
              100                     105                      110

Val  Phe  Ser  Val  Cys  Arg  Ile  Met  Gly  Trp  Gly  Thr  Ile  Thr  Ser  Pro
         115                      120                 125

Gln  Val  Thr  Phe  Pro  Asp  Val  Leu  His  Cys  Ala  Asn  Ile  Asn  Ile  Phe
     130                      135                 140

Asp  Tyr  Glu  Val  Cys  Arg  Ala  Ala  Tyr  Pro  Glu  Leu  Pro  Ala  Thr  Arg
145                      150                 155                           160

Arg  Thr  Leu  Cys  Ala  Gly  Ile  Leu  Glu  Gly  Gly  Lys  Asp  Ser  Cys  Gln
                    165                 170                           175

Gly  Asp  Ser  Gly  Gly  Pro  Leu  Ile  Cys  Asn  Gly  Gln  Phe  Gln  Gly  Ile
               180                      185                      190

Ala  Tyr  Trp  Gly  Ala  Asp  Thr  Cys  Ala  Gln  Pro  Arg  Glu  Pro  Gly  Leu
          195                      200                      205

Tyr  Thr  Lys  Val  Phe  Asp  Tyr  Ile  Asp  Trp  Ile  Gln  Ser  Ile  Ile  Ala
          210                 215                      220

Gly  Asn  Thr  Ala  Val  Thr  Cys  Pro  Pro
225                      230
```

( 2 ) INFORMATION FOR SEQ ID NO:10:

( i ) SEQUENCE CHARACTERISTICS:
         ( A ) LENGTH: 236 amino acids
         ( B ) TYPE: amino acid
         ( C ) STRANDEDNESS: Not Relevant
         ( D ) TOPOLOGY: Not Relevant ( i i ) MOLECULE TYPE: protein ( v i ) ORIGINAL SOURCE:
         ( A ) ORGANISM: Trimeresurus flavoviridis ( v i i ) IMMEDIATE SOURCE:
         ( B ) CLONE: FLAVOXOBIN ( x i ) SEQUENCE DESCRIPTION: SEQ ID NO:10:

```
Val  Ile  Gly  Gly  Asp  Glu  Cys  Asp  Ile  Asn  Glu  His  Pro  Phe  Leu  Val
1                   5                      10                      15

Ala  Leu  Tyr  Asp  Ala  Trp  Ser  Gly  Arg  Phe  Leu  Cys  Gly  Gly  Thr  Leu
               20                  25                           30

Ile  Asn  Pro  Glu  Trp  Val  Leu  Thr  Ala  Ala  His  Cys  Asp  Ser  Lys  Asn
          35                      40                 45

Phe  Lys  Met  Lys  Leu  Gly  Ala  His  Ser  Gln  Lys  Val  Leu  Asn  Glu  Asp
     50                      55                 60

Glu  Gln  Ile  Arg  Asn  Pro  Lys  Glu  Lys  Phe  Ile  Cys  Pro  Asn  Lys  Lys
65                       70                 75                           80

Asn  Thr  Glu  Val  Leu  Asp  Lys  Asp  Ile  Met  Leu  Ile  Lys  Leu  Asp  Ser
                    85                      90                      95

Pro  Val  Ser  Tyr  Ser  Glu  His  Ile  Ala  Pro  Leu  Ser  Leu  Pro  Ser  Ser
              100                     105                      110

Pro  Pro  Ser  Val  Gly  Ser  Val  Cys  Arg  Ile  Met  Gly  Trp  Gly  Ser  Ile
         115                      120                 125

Thr  Pro  Val  Glu  Glu  Thr  Phe  Pro  Asp  Val  Pro  His  Cys  Ala  Asn  Ile
     130                      135                 140

Asn  Leu  Leu  Asp  Asp  Val  Glu  Cys  Lys  Pro  Gly  Tyr  Pro  Glu  Leu  Leu
145                      150                 155                           160

Pro  Glu  Tyr  Arg  Thr  Leu  Cys  Ala  Gly  Val  Leu  Gln  Gly  Gly  Ile  Asp
```

|     |     |     |     |     | 165 |     |     |     | 170 |     |     |     |     | 175 |
|-----|-----|-----|-----|-----|-----|-----|-----|-----|-----|-----|-----|-----|-----|-----|

Thr Cys Gly Phe Asp Ser Gly Thr Pro Leu Ile Cys Asn Gly Gln Phe
                180                185                190

Gln Gly Ile Val Tyr Ile Gly Ser His Pro Cys Gly Gln Ser Arg Lys
            195                200                205

Pro Gly Ile Tyr Thr Lys Phe Asp His Tyr Asn Ala Trp Ile Gln Ser
        210                215                220

Ile Ile Ala Gly Asn Thr Ala Ala Thr Cys Lys Pro
225                 230                 235

( 2 ) INFORMATION FOR SEQ ID NO:11:

( i ) SEQUENCE CHARACTERISTICS:
        ( A ) LENGTH: 232 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Bothrops atrox moojeni ( v i i ) IMMEDIATE SOURCE:
        ( B ) CLONE: BATROXOBIN ( x i ) SEQUENCE DESCRIPTION: SEQ ID NO:11:

Val Ile Gly Gly Asp Glu Cys Asp Ile Asn Glu His Pro Phe Leu Ala
1               5                  10                 15

Phe Met Tyr Tyr Ser Pro Arg Tyr Phe Cys Gly Met Thr Leu Ile Asn
            20                 25                 30

Gln Glu Trp Val Leu Thr Ala Ala His Cys Asn Arg Arg Phe Met Arg
        35                 40                 45

Ile His Leu Gly Lys His Ala Gly Ser Val Ala Asn Tyr Asp Glu Val
    50                 55                 60

Val Arg Tyr Pro Lys Glu Lys Phe Ile Cys Pro Asn Lys Lys Lys Asn
65                  70                 75                  80

Val Ile Thr Asp Lys Asp Ile Met Leu Ile Arg Leu Asp Arg Pro Val
            85                 90                 95

Lys Asn Ser Glu His Ile Ala Pro Leu Ser Leu Pro Ser Asn Pro Pro
            100                105                110

Ser Val Gly Ser Val Cys Arg Ile Met Gly Trp Gly Ala Ile Thr Thr
        115                120                125

Ser Glu Asp Thr Tyr Pro Asp Val Pro His Cys Ala Asn Ile Asn Leu
    130                135                140

Phe Met Asn Thr Val Cys Arg Glu Ala Tyr Asn Gly Leu Pro Ala Lys
145                 150                155                 160

Thr Leu Cys Ala Gly Val Leu Gln Gly Gly Ile Asp Thr Cys Gly Gly
            165                170                175

Asp Ser Gly Gly Pro Leu Ile Cys Asn Gly Gln Phe Gln Gly Ile Leu
        180                185                190

Ser Trp Gly Ser Asp Pro Cys Ala Glu Pro Arg Lys Pro Ala Phe Tyr
    195                200                205

Thr Lys Phe Asp His Tyr Leu Pro Trp Ile Gln Ser Ile Ile Ala Gly
    210                215                220

Asn Lys Thr Ala Thr Cys Pro Pro
225                 230

( 2 ) INFORMATION FOR SEQ ID NO:12:

(i) SEQUENCE CHARACTERISTICS:
  (A) LENGTH: 234 amino acids
  (B) TYPE: amino acid
  (C) STRANDEDNESS: Not Relevant
  (D) TOPOLOGY: Not Relevant (ii) MOLECULE TYPE: protein (vi) ORIGINAL SOURCE:
  (A) ORGANISM: Calloselasma rhodostoma (vii) IMMEDIATE SOURCE:
  (B) CLONE: ANCROD (xi) SEQUENCE DESCRIPTION: SEQ ID NO:12:

```
Val  Ile  Gly  Gly  Asp  Glu  Cys  Asp  Ile  Asn  Glu  His  Arg  Phe  Leu  Val
 1              5                        10                       15

Ala  Val  Tyr  Glu  Gly  Thr  Asn  Trp  Thr  Phe  Ile  Cys  Gly  Gly  Val  Leu
               20                       25                  30

Ile  His  Pro  Glu  Trp  Val  Leu  Thr  Ala  Glu  His  Cys  Ala  Arg  Arg  Arg
               35                       40                  45

Met  Asn  Leu  Val  Phe  Gly  Met  His  Arg  Lys  Ser  Glu  Lys  Phe  Asp  Asp
      50                        55                  60

Glu  Gln  Glu  Arg  Tyr  Pro  Lys  Lys  Arg  Tyr  Phe  Ile  Arg  Cys  Asn  Lys
 65                       70                       75                       80

Thr  Arg  Thr  Ser  Trp  Asp  Glu  Asp  Ile  Met  Leu  Ile  Arg  Leu  Asn  Lys
                    85                        90                            95

Pro  Val  Asn  Asn  Ser  Glu  His  Ile  Ala  Pro  Leu  Ser  Leu  Pro  Ser  Asn
               100                      105                 110

Pro  Pro  Ile  Val  Gly  Ser  Val  Cys  Arg  Ile  Met  Gly  Trp  Gly  Ser  Ile
           115                      120                 125

Asn  Arg  Arg  Ile  Asp  Val  Leu  Ser  Asp  Glu  Pro  Arg  Cys  Ala  Asn  Ile
     130                      135                 140

Asn  Leu  His  Asn  Phe  Thr  Met  Cys  His  Gly  Leu  Phe  Arg  Lys  Met  Pro
145                      150                 155                      160

Lys  Lys  Gly  Arg  Val  Leu  Cys  Ala  Gly  Asp  Leu  Arg  Gly  Arg  Arg  Asp
                165                      170                      175

Ser  Cys  Asn  Ser  Asp  Ser  Gly  Gly  Pro  Leu  Ile  Cys  Asn  Glu  Glu  Leu
               180                      185                 190

His  Gly  Ile  Val  Ala  Arg  Gly  Pro  Asn  Pro  Cys  Ala  Gln  Pro  Asn  Lys
           195                      200                 205

Pro  Ala  Leu  Tyr  Thr  Ser  Ile  Tyr  His  Tyr  Arg  Asp  Trp  Val  Asn  Asn
     210                      215                 220

Val  Ile  Ala  Gly  Asn  Ala  Thr  Cys  Ser  Pro
225                 230
```

What is claimed is:

1. A cDNA of a direct-acting fibrinolytic serine protease, which is originated from a cDNA library of the venom gland of *Agkistrodon halys* brevicaudus and whose nucleotide sequence is represented as following (SEQ ID No: 8):

| | | | |
|---|---|---|---|
| GTCATTGGAG | GAGACGAATG | TAACATAAAT | 50 |
| | GAACATCGTT | TCCTTGCACT | |
| CCTGTACTCT | GAGAGGTTTC | AATGCGGTGG | 100 |
| | GACTTTGATC | AACGAAGAAT | |
| GGGTGCTCAC | CGCTGCACAC | TGCGACATGA | 150 |
| | GAAATATGTA | CATATACCTT | |
| GGTGTGCATA | ACGTAAGTGT | ACAATACGAT | 200 |
| AAAGAAGAAG | GATGAGCAGA | GAAGATACCC | |
| | CACTTTCGCC | TCAGTAGCAG | 250 |
| | | AAACTATAAC | CAATGGGACA |
| AGGATATCAT | GTTGATCAGA | TTGAACAGAC | 300 |
| | | CTCTTAGGAA | CAGTGCACAC |
| ATCGCGCCTC | TCAGCTTGCC | TTCCAACCCT | 350 |
| | | CCCAGTGTGT | TCTCAGTTTG |
| CCGTATTATG | GGATGGGGCA | CAATCACATC | 400 |
| | | TCCTCAAGTG | ACTTTTCCCG |
| ATGTCCTTCA | CTGTGCTAAC | ATTAACATTT | 450 |
| | | TTGATTATGA | GGTGTGTCGA |
| GCAGCTTACC | CAGAGTTGCC | AGCAACAAGG | 500 |
| | | AGAACATTGT | GTGCAGGTAT |

-continued

```
CCTGGAAGGA  GGCAAAGATT  CATGTAACGG            550
            TGACTCTGGG  GGACCCCTCA
TCTGTAATGG  ACAATTCCAG  GGCATTGCAT            600
            ATTGGGGGGC  CGATACTTGT
GCCCAACCGC  GTGAGCCTGG  CCTCTACACC            650
            AAGGTCTTTG  ATTATATTGA
TTGGATCCAA  AGCATTATTG  CAGGAAATAC            699
            AGCTGTGACT  TGCCCCCCA
```

2. The cDNA of claim 1, which is cloned from the cDNA library of the venom gland of *Agkistrodon halys* brevicaudus employing primers of two pairs of oligonucleotides as following:

5' primer: 5'-AA(T/C)TA(T/C)AA(T/C)CA(A/G)TTG-3' (SEQ ID No: 1)

3' primer: 5'-AT(A/T/G)ATGCT(C/T)TG(A/T/G)CA(A/G)TC-3' (SEQ ID No: 3); and,

5' primer: 5'-GTIATIGGIGGNGA(T/C)GA(A/G)TG-3' (SEQ ID No: 5)

3' primer: 5'-TT(A/G)AT(A/G)TT(A/G)GT(T/C)AAC-3' (SEQ ID No: 7)

wherein,

I represents inosine; and,

N represents A, G, C or T.

3. An isolated direct-acting fibrinolytic serine protease having a molecular weight of about 26 kDa and isoelectric point(pI) of 5.04, which has the following amino acid sequence (SEQ ID No: 9) deduced from the cDNA of claim 1:

|   |   |   |   | 5 |   |   |   |   | 10 |   |   |   |   | 15 |   |   |   |   | 20 |   |   |   |   | 25 |     |
|---|---|---|---|---|---|---|---|---|----|---|---|---|---|----|---|---|---|---|----|---|---|---|---|----|-----|
| V | I | G | G | D | E | C | N | I | N  | E | H | R | F | L  | A | L | L | Y | S  | E | R | F | Q | C  | 25  |
| G | G | T | L | I | N | E | E | W | V  | L | T | A | A | H  | C | D | M | R | N  | M | Y | I | Y | L  | 50  |
| G | V | H | N | V | S | V | Q | Y | D  | D | E | Q | R | R  | Y | P | K | K | K  | Y | F | R | L | S  | 75  |
| S | R | N | Y | N | Q | W | D | K | D  | I | M | L | I | R  | L | N | R | P | L  | R | N | S | A | H  | 100 |
| I | A | P | L | S | L | P | S | N | P  | P | S | V | F | S  | V | C | R | I | M  | G | W | G | T | I  | 125 |
| T | S | P | Q | V | T | F | P | D | V  | L | H | C | A | N  | I | N | I | F | D  | Y | E | V | C | R  | 150 |
| A | A | Y | P | E | L | P | A | T | R  | R | T | L | C | A  | G | I | L | E | G  | G | K | D | S | C  | 175 |
| Q | G | D | S | G | G | P | L | I | C  | N | G | Q | F | Q  | G | I | A | Y | W  | G | A | D | T | C  | 200 |
| A | Q | P | R | E | P | G | L | Y | T  | K | V | F | D | Y  | I | D | W | I | Q  | S | I | I | A | G  | 225 |
| N | T | A | V | T | C | P | P |   |    |   |   |   |   |    |   |   |   |   |    |   |   |   |   |    | 233 |

4. The direct-acting fibrinolytic serine protease of claim 3 which consists of two subunits resulting from proleolytic cleavage between the 77th amino acid, Arg and the 78th amino acid, Asn.

* * * * *